United States Patent [19]

Mittermeier et al.

[11] Patent Number: 5,403,844
[45] Date of Patent: Apr. 4, 1995

[54] MICROBICIDES

[75] Inventors: Ludwig Mittermeier, Freiburg, Germany; Wilhelm Ruess, Pfeffingen, Switzerland

[73] Assignee: Ciba-Geigy Corporation, Ardsley, N.Y.

[21] Appl. No.: 991,674

[22] Filed: Dec. 16, 1992

[30] Foreign Application Priority Data

Dec. 19, 1991 [CH] Switzerland .................. 3780/91

[51] Int. Cl.$^6$ ................ A01N 43/54; A01N 43/64
[52] U.S. Cl. ........................... 514/275; 514/383
[58] Field of Search .................... 514/383, 275

[56] References Cited

U.S. PATENT DOCUMENTS

| | | | |
|---|---|---|---|
| 3,952,002 | 4/1976 | Kramer et al. | 260/308 R |
| 4,510,136 | 4/1985 | Moberg | 514/63 |
| 4,532,341 | 7/1985 | Holmwood et al. | 549/559 |
| 4,626,595 | 12/1986 | Holmwood et al. | 549/559 |
| 4,652,580 | 3/1987 | Janssen et al. | 514/383 |
| 4,664,696 | 5/1987 | Schaub | 71/92 |
| 4,723,984 | 2/1988 | Holmwood et al. | 71/76 |
| 4,789,672 | 12/1988 | Holmwood et al. | 514/184 |
| 4,871,390 | 10/1989 | Holmwood et al. | 71/92 |
| 4,897,107 | 1/1990 | Holmwood et al. | 71/92 |
| 4,904,298 | 2/1990 | Holmwood et al. | 71/92 |
| 4,906,652 | 3/1990 | Karbach et al. | 514/383 |
| 4,911,746 | 3/1990 | Holmwood et al. | 71/92 |
| 4,931,560 | 6/1990 | Hubele | 544/315 |
| 4,997,941 | 3/1991 | Hubele | 544/332 |
| 5,153,200 | 10/1992 | Hubele | 514/275 |

FOREIGN PATENT DOCUMENTS

| | | |
|---|---|---|
| 0015756 | 9/1980 | European Pat. Off. . |
| 0251775 | 1/1988 | European Pat. Off. . |
| 1522657 | 8/1978 | United Kingdom . |
| 2098607 | 11/1982 | United Kingdom . |
| 2119653 | 11/1983 | United Kingdom . |

*Primary Examiner*—Allen J. Robinson
*Attorney, Agent, or Firm*—Edward McC. Roberts

[57] ABSTRACT

Mixtures of certain triazole fungicides (component I) and 4-cyclopropyl-6-methyl-N-phenyl-2-pyrimidinamine (component II) have a synergistically increased activity against fungus infestation. Components I and II can also be applied to crops individually in immediate succession.

12 Claims, No Drawings

MICROBICIDES

The present invention relates to fungicidal two-component mixtures having a synergistically increased action and to methods for using such mixtures in crop protection.

Component I is an ergosterin biosynthesis inhibitor from the triazole series or one of the salts or metal complexes thereof, selected from amongst A) 1-[2-(2,4-dichlorophenyl)-4-propyl-1,3-dioxolan-2-ylmethyl]-1H-1,2,4-triazole, commercial name propiconazole, (Reference: GB-1 522 657);

B) 1-{2-[2-chloro-4-(4-chlorophenoxy)-phenyl]-4-methyl-1,3-dioxolan-2-ylmethyl {-1H-1,2,4-triazole, commercial name difenoconazole, (Reference: GB-2 098 607);

C) α-[2-(4-chlorophenyl)ethyl]α-(1,1-dimethylethyl)-1H-1,2,4-triazol-1-ethanol, commercial name tebuconazole, (Reference: EP-A-40 345);

D) 1-(4-chlorophenoxy)-3,3-dimethyl-1-(1,2,4-triazol-1-yl)-butan-2-ol, commercial name triadimenol, (Reference: German Offenlegungsschrift 2 324 010);

E) 1-[3-(2-chlorophenyl)-2-(4-fluorophenyl)oxiran-2-ylmethyl]-1H-1,2,4-triazole, cod name BAS-480-F, (Reference EP-A-196 038);

F) α-(4-chlorophenyl)-α-(1-cyclopropylethyl)-1H-1,2,4-triazol-1-ethanol, commercial name cyproconazole (Reference: U.S. Pat. No. 4,664,696);

G) 4-(4-chlorophenyl)-2-phenyl-2-(1,2,4-triazol-1-ylmethyl)-butyronitrile, proposed commercial name fenbuconazole (Reference: EP-A-251 775);

H) α-(2-fluorophenyl)-α-(4-fluorophenyl)-1H-1,2,4-triazol-1-ethanol, commercial name flutriafol (Reference: EP-A-15 756);

J) α-butyl-α-(2,4-dichlorophenyl)-1H-1,2,4-triazol-1-ethanol, commercial name hexaconazole (Reference: GB-2 119 653); and K) 1-{[bis(4-fluorophenyl)methylsilyl]methyl }-1H-1,2,4-triazole, commercial name flusilazole (Reference: U.S. Pat. No. 4,510,136).

Component II is the 2-anilinopyrimidine of the formula

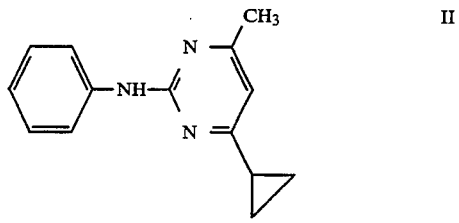

4-cyclopropyl-6-methyl-N-phenyl-2-pyrimidinamine or a salt or metal complex thereof (Reference: EP-A-310 550).

The following may be mentioned as examples of acids which can be used for preparing salts of the formula I or II:

Hydrohalic acids such as hydrofluoric acid, hydrochloric acid, hydrobromic acid or hydriodic acid, as well as sulfuric acid, phosphoric acid, nitric acid and organic acids such as acetic acid, trifluoroacetic acid, trichloroacetic acid, propionic acid, glycolic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid, 2-acetoxybenzoic acid or 1,2-naphthalenedisulfonic acid.

The term salts also includes metal complexes of the two basic components I and II. These complexes can apply to one component only or, alternatively, independently to both components. It is also possible to prepare metal complexes in which the two active ingredients I and II are combined with each other to form a mixed complex.

Metal complexes are composed of the organic molecule on which they are based and an inorganic or organic metal salt, for example the halides, nitrates, sulfates, phosphates, acetates, trifluoroacetates, trichloroacetates, propionates, tartrates, sulfonates, salicylates, benzoates etc. of the elements of the second main group such as calcium and magnesium and of the third and fourth main groups such as aluminium, tin or lead, and the first to eighth subgroups such as chromium, manganese, iron, cobalt, nickel, copper, zinc etc. The subgroup elements of the 4th period are preferred. The metals can exist in the various valencies which they can assume. The metal complexes can be mono- or polynuclear, i.e. they can contain one or more organic moieties as ligands, such as in the case of the abovementioned mixed complexes of triazole component I and anilinopyrimidine II.

The triazole components I can exist in stereoisomeric forms or as racemates. While components IC and IG to IJ can form two stereoisomers, four stereoisomers are possible for each of the remaining components IA (propiconazole), IB (difenoconazole), ID (triadimenol), IE (BAS-480-F) and IF (cyproconazole). The different isomeric forms of one of the preparations can differ in their fungicidal activity. In the case of propiconazole, for example, the two cis isomers are preferred, i.e. those enantiomers in which the triazolylmethyl group and the propyl group are on the same side of the dioxolane ring. In the case of B AS-480-F, the two Z (=cis) enantiomers are preferred.

For use in practise, it is advantageous to use the active ingredients I and II as free bases and in racemate form, and further agrochemical active ingredients such as insecticides, acaricides, nematicides, herbicides, growth regulators and fertilizers, but in particular other microbicides, can be added.

In recent years, so-called ergosterin biosynthesis inhibitors have increased their market share, i.e. preparations whose fungicidal action is based on inhibiting the biosynthesis of ergosterin, which can be found in the cell membrane of fungi. As a rule, fungicides which contain a 1H-1,2,4-triazole radical in the molecule act as a 14-C demethylation inhibitor (=DMI) in this process. However, in some areas fungal strains have been found where a reduction in sensitivity has been proved, due to the long-term use of preparations on the basis of triazole.

Surprisingly, it has now emerged that mixtures of components I with the anilinopyrimidine II not only exhibit an additive activity with regard to their fungicidal action, but also show a clear, synergistically increased activity even in the case of fungal isolates which have acquired a reduced sensitivity to triazole fungicides.

The present invention is therefore an essential enrichment of the art.

The present invention relates not only to the two-component mixture but also to a method of controlling fungi which comprises treating a locus infested with, or endangered by, fungi in any desired sequence or simultaneously with a) one of the components I or a (metal) salt thereof and b) with the active ingredient of the formula II or a salt thereof, it also being possible for the salts to be selected in such a way that both active ingredients are bonded to an acid radical or, in the case of a metal complex, to a central metal cation.

Advantageous mixing ratios of the two active ingredients are I:II = 10:1 to 1:20, preferably I:II = 6:1 to 1:6. Mixtures in which the mixing ratio of the pure active ingredients I:II = 1:1 to 1:6 for example 2:5, 1:3, 1:4 or 1:6, are frequently advantageous.

The active ingredient mixtures I+II according to the invention have very advantageous curative, preventive and systemic fungicidal properties for protecting crop plants. The active ingredient mixtures provided can be used for containing or destroying the microorganisms which occur on plants or parts of plants (fruits, flowers, foliage, stalks, tubers, roots) of a range of crops of useful plants, and even newly-forming parts of the plants remain unharmed by such microorganisms. This applies, in particular, to microorganisms which have developed a reduced sensitivity to fungicides from the class of the triazoles.

The active ingredient mixtures are effective against the phytopathogenic fungi belonging to the following classes: Ascomyceten (for example Venturia, Podosphaera, Erysiphe, Monilinia, Uncinula); Basidiomyceten (for example the genus Hemileia, Rhizoctonia, Puccinia); Fungi imperfecti (for example Botrytis, Helminthosporium, Rhynchosporium, Fusarium, Septoria, Cercospora, Alternaria, Pyricularia and, in particular, Pseudocercosporella herpotrichoides). The active ingredient mixtures are systemically-acting. They can also be used as seed-dressing agents for the treatment of seed (fruits, tubers, kernels) and cuttings for protecting against fungal infections and against soil-borne phytopathogenic fungi. The active ingredient mixtures according to the invention are distinguished by the fact that they are environmentally friendly and particularly well tolerated by plants.

Target crops for the indications disclosed herein are, within the scope of the present invention, for example the following plant species: cereals: (wheat, barley, rye, oats, rice, sorghum and related species); beet: (sugar beet and fodder beet); pomaceous fruit, stone fruit and soft fruit: (apples, pears, plums, peaches, almonds, cherries, strawberries, raspberries and blackberries); pulses: (beans, lentils, peas, soya beans); oil crops: (oil seed rape, mustard, poppy, olives, sunflowers, coconut, castor-oil plant, cacao, groundnuts); cucurbits: (pumpkin, cucumbers, melons); fibre plants: (cotton, flax, hemp, jute); citrus fruit: (oranges, lemons, grapefruit, tangerines); various vegetables (spinach, lettuce, asparagus, cabbage species, carrots, onions, tomatoes, potatoes, bell peppers); Lauraceae: (avocado, cinnamonum, camphor) or plants such as maize, tobacco, nuts, coffee, sugar cane, tea, grape vines, hops, Musaceae and natural latex plants as well as ornamentals (flowers, shrubs, deciduous trees and coniferous trees such as conifers). This enumeration does not represent a limitation.

The active ingredient mixtures of the formulae I and II are customarily used in the form of combinations. The active ingredients of the formula I and the active ingredient of the formula II can be applied to the area or plant to be treated either simultaneously or in succession on the same day, if desired together with other carders, surfactants or application-enhancing additives conventionally used in the art of formulation.

Suitable carders and additives can be solid or liquid and are those substances which are expedient in the art of formulation, for example natural or regenerated mineral substances, solvents, dispersants, wetting agents, adhesives, thickeners, binders or fertilizers.

A preferred method for applying an active ingredient mixture comprising at least in each case one of these active ingredients I and II is application to the aerial parts of the plants, especially the foliage (foliar application). The number of applications and the application rate depend on the biological and climatic environment of the pathogen. Alternatively, the active ingredients can reach the plant via the soil by means of the roots (systemic action), by drenching the locus of the plant with a liquid preparation or by incorporating the substances into the soil in solid form, for example in the form of granules (soil application). The compounds of the formulae I and II can also be applied to seeds (coating), either by soaking the kernels in succession with a liquid preparation of an active ingredient or by applying a layer of a moist or dry preparation which has already been combined. Moreover, other ways of applying them to plants are possible in special cases, for example the targeted treatment of the buds or the inflorescence.

The compounds of the combination are employed as pure active ingredients or, preferably, together with the auxiliaries conventionally used in the art of formulation. They are therefore processed in the known manner to give, for example, emulsion concentrates, spreadable pastes, directly sprayable or dilutable solutions, dilute emulsions, wettable powders, soluble powders, dusts, granules, or encapsulations, for example in polymeric substances. The application methods such as spraying, atomising, dusting, scattering, brushing on or pouring, as well as the nature of the compositions, are selected to suit the intended aims and the prevailing circumstances. Favourable application rates of the active ingredient mixture are generally 50 g to 2 kg of AI/ha, in particular 100 g to 1000 g of AI/ha, particularly preferably 250 g to 850 g of AI/ha.

The formulations are produced in the known manner, for example by intimately mixing and/or grinding the active ingredients with extenders, for example with solvents, solid carriers and, if appropriate, surface-active compounds (surfactants).

The following are possible as solvents: aromatic hydrocarbons, preferably the fractions $C_8$ to $C_{12}$, for example xylene mixtures or substituted naphthalenes, phthalic esters such as dibutyl phthalate or dioctyl phthalate, aliphatic hydrocarbons such as cyclohexane or paraffins, alcohols and glycols as well as their ethers and esters, such as ethanol, ethylene glycol, ethylene glycol monomethyl ether or ethylene glycol monoethyl ether, ketones such as cyclohexanone, strongly polar solvents such as N-methyl-2-pyrrolidone, dimethylsulfoxide or dimethylformamide, and also epoxidised or unexpoxidised vegetable oils such as epoxidised coconut oil or soya oil; or water.

Solid carders which are used, for example for dusts and dispersible powders, are, as a rule, ground natural minerals such as calcite, talc, kaolin, montmorillonite or attapulgite. To improve the physical properties, it is also possible to add highly-disperse silica or highly-disperse absorptive polymers. Possible particulate, adsorptive carders for granules are porous types, such as pumice, brick grit, sepiolite or bentonite, and suitable non-sorptive carder materials are, for example, calcite or sand. Moreover, a large number of pregranulated materials of inorganic or organic nature can be used such as, in particular, dolomite or comminuted plant residues.

Suitable surface-active compounds are non-ionic, cationic and/or anionic surfactants which have good emulsifying, dispersing and wetting properties, depending on the nature of the active ingredients of the formulae I and II to be formulated. Surfactants are also to be understood as meaning mixtures of surfactants.

The surfactants conventionally used in the art of formulation have been published, inter alia, in the following:

"Mc Cutcheon's Detergents and Emulsifiers Annual" MC Publishing Corp., Glen Rock, N.J., 1988.

M. and J. Ash, "Encyclopedia of Surfactants", Vol. I-III, Chemical Publishing Co., New York, 1980–1981.

Particularly advantageous adjuvants which enhance application are furthermore natural or synthetic phospholipids from the series of the cephalins and lecithins, such as phosphatidylethanolamine, phosphatidylserine, phosphatidylglycerol, lysolecithin.

As a rule, the agrochemical preparations comprise 0.1 to 99 %, in particular 0.1 to 95 %, of active ingredients of the formulas I and II, 99.9 to 1%, in particular 99.9 to 5 %, of a solid or liquid additive and 0 to 25 %, in particular 0.1 to 25 %, of a surfactant.

While concentrated compositions are more preferred as commercially available goods, the end consumer uses, as a rule, dilute compositions.

Such (agro)chemicals are part of the present invention.

The examples which follow are intended to illustrate the invention, and "active ingredient" is to be understood as meaning a mixture of compound I and compound II in a particular mixing ratio.

| Wettable powders | a) | b) | c) |
|---|---|---|---|
| Active ingredient [I:II = 2:3(a), 1:1(b), 1:6(c)] | 25% | 50% | 75% |
| Sodium ligninsulfonate | 5% | 5% | — |
| Sodium lauryl sulfate | 3% | — | 5% |
| Sodium diisobutylnaphthalene sulfonate | — | 6% | 10% |
| Octylphenol polyethylene glycol ether (7–8 moles of ethylene oxide) | — | 2% | — |
| Highly-disperse silica | 5% | 10% | 10% |
| Kaolin | 62% | 27% | — |

The active ingredient is mixed thoroughly with the additives and the mixture is ground thoroughly in a suitable mill. This gives wettable powders which can be diluted with water to give suspensions of any desired concentration.

| Emulsion concentrate | |
|---|---|
| Active ingredient (I:II = 2:5) | 10% |
| Octylphenol polyethylene glycol ether (4–5 moles of ethylene oxide) | 3% |
| Calcium dodecylbenzenesulfonate | 3% |
| Castor oil polyglycol ether (35 moles of ethylene oxide) | 4% |
| Cyclohexanone | 30% |
| Xylene mixture | 50% |

Emulsions of any desired dilution which can be used in crop protection can be prepared from this concentrate by diluting with water.

| Dusts | a) | b) | c) |
|---|---|---|---|
| Active ingredient [I:II = 1:4(a), 1:5(b) and 1:1 (c)] | 5% | 6% | 4% |
| Talc | 95% | — | — |
| Kaolin | — | 94% | — |
| Ground minerals | — | — | 96% |

Ready-for-use dusts are obtained by mixing the active ingredient with the carrier and grinding the mixture in a suitable mill. Such powders can also be used as a composition for dry-dressing seeds.

| Extruder granules | |
|---|---|
| Active ingredient (I:II = 2:3) | 15% |
| Sodium ligninsulfonate | 2% |
| Carboxymethylcellulose | 1% |
| Kaolin | 82% |

The active ingredient is mixed with the additives, and the mixture is ground and moistened with water. This mixture is extruded and subsequently dried in a stream of air.

| Coated granules | |
|---|---|
| Active ingredient (I:II = 3:5) | 8% |
| Polyethylene glycol (MW 200) | 3% |
| Kaolin | 89% |
| (MW = molecular weight) | |

In a mixer, the finely-ground active ingredient is applied uniformly to the kaolin which has been moistened with polyethylene glycol. In this manner, dust-free coated granules are obtained.

| Suspension concentrate | |
|---|---|
| Active ingedient (I:II = 3:7) | 40% |
| Propylene glycol | 10% |
| Nonylphenol polyethylene glycol ether (15 moles of ethylene oxide) | 6% |
| Sodium ligninsulfonate | 10% |
| Carboxymethyl cellulose | 1% |
| Silicone oil (in the form of a 75% aqueous emulsion) | 1% |
| Water | 32% |

The finely-ground active ingredient is mixed intimately with the additives. This gives a suspension concentrate from which suspensions of any desired dilution can be prepared by diluting it with water. Live plants and plant propagation material can be treated and protected from infestation with microorganisms by spraying them with such dilutions, pouring such dilutions or immersing the live plants or plant propagation material in such dilutions.

BIOLOGICAL EXAMPLES

A synergistic effect in fungicides is always present when the fungicidal activity of the active ingredient combination exceeds the total of the activities of the individually applied active ingredients.

The activity E to be expected for a given active ingredient combination, for example of two fungicides, follows the so-called COLBY formula and can be calculated as follows (COLBY, L.R. "Calculating synergistic and antagonistic responses of herbicide combinations". Weeds 15, pages 20-22, 1967) (LIMPEL and al., 1062 "Weeds control by certain combinations". Proc. NEWCL, Vol. 16, pp. 48-53): (g of AS/ha = grams of active ingredient per hectare) if X = % activity of fungicide I at p g of AS/ha
Y = % activity of fungicide II at q g of AS/ha
E = the expected activity of fungicides I+II at an application rate of p+q g AS/ha (additive action), then Colby's formula reads:

$$E = X + Y - \frac{X \cdot Y}{100}$$

If the observed activity (O) exceeds the expected activity, then the combination is super additive in its activity, i.e. a synergistic effect exists.

EXAMPLE 1

Action against "powdery mildew" on winter wheat

Method:

Approx. 20 winter wheat plants cv. "Bernina" are grown in the greenhouse in pots of diameter 16 cm at 20° C. and 60 % relative atmospheric humidity during a 12 hour day and 16° C and 80 % relative atmospheric humidity during the night. At the beginning of tillering (EC 21), the plants are inoculated with an isolate of Erysiphe graminis f. sp. tritici which has a reduced sensitivity to DMI fungicides.

3 days after inoculation, the individual active ingredient, or the fungicide mixture, in the form of an aqueous suspension is applied under field conditions using a spray boom and an application rate of 500 l of water/ha. The change in infestation on the leaf area present during inoculation is determined 4 days or 11 days after application (evaluation of the primary infestation). Each of the 15 experiments is replicated 3 times.

The application rates shown in Tables 1a and 2a are used.

The following results are obtained with mixtures composed of IA (=propiconazole) and II:

TABLE 1 a

Evaluation 7 days after the experiment was set up (active ingredient IA = propiconazole)

| Exp. No. | g of active ingredient/ha AI I | g of active ingredient/ha AI II | Fungus infestation in % | E % activity, calculated [COLBY] | O % activity, found |
|---|---|---|---|---|---|
| 1 (control) | — | — | 38 | — | |
| 2 | 25 | — | 35 | — | 8 |
| 3 | 50 | — | 24 | — | 37 |
| 4 | 125 | — | 3 | — | 92 |
| 5 | — | 25 | 30 | — | 21 |
| 6 | — | 50 | 15 | — | 61 |
| 7 | — | 125 | 10 | — | 74 |
| 8 | — | 750 | 7 | — | 82 |
| 9 | 25 | 25 | 16 | 27 | 58 |
| 10 | 25 | 50 | 11 | 64 | 71 |
| 11 | 25 | 125 | 4 | 76 | 89 |
| 12 | 50 | 25 | 10 | 50 | 74 |
| 13 | 50 | 50 | 4 | 75 | 90 |
| 14 | 50 | 125 | 5 | 84 | 87 |
| 15 | 125 | 25 | 2 | 94 | 95 |

TABLE 1b

Evaluation 14 days after the experiment was set up (active ingredient IA = propiconazole)

| Exp. No. | g of active ingredient/ha AI I | g of active ingredient/ha AI II | Fungus infestation in % | E % activity, calculated [COLBY] | O % activity, found |
|---|---|---|---|---|---|
| 1 (control) | — | — | 83 | — | |
| 2 | 25 | — | 85 | — | 2 |
| 3 | 50 | — | 68 | — | 18 |
| 4 | 125 | — | 14 | — | 83 |
| 5 | — | 25 | 78 | — | 6 |
| 6 | — | 50 | 80 | — | 4 |
| 7 | — | 125 | 55 | — | 34 |
| 8 | — | 750 | 3 | — | 96 |
| 9 | 25 | 25 | 73 | 5 | 12 |
| 10 | 25 | 50 | 78 | 1 | 6 |
| 11 | 25 | 125 | 33 | 33 | 60 |
| 12 | 50 | 25 | 53 | 23 | 36 |
| 13 | 50 | 50 | 37 | 21 | 55 |
| 14 | 50 | 125 | 40 | 46 | 52 |
| 15 | 125 | 25 | 7 | 84 | 92 |

As can be seen, quite different mixing ratios result in a synergistically increased fungicidal activity in Experiments No. 9 to 15, after 7 as well as 14 days.

EXAMPLE 2

Activity against "Septoria nodorum" (wheat)

Method:

Septoria nodorum is gown for 2 weeks on agar plates on a nutrient medium composed of 1 g of dry yeast, 20 g of wheat flour and 20 g of agar per liter of water. To induce sporulation, the fungus is placed into a jar filled with wheat kernels and incubated for 4 weeks at 8° C. (simulated 16-hour day). The spores formed are then washed out with water and filtered, and the suspension is adjusted to a concentration of 10 000 spores/ml (concentration in microtitre plates).

Microtitre plates with 96 wells are used for measuring the activity of the fungicides and fungicide mixtures. Using a Hamilton pipette, 180 µl PDB medium (potato dextrose broth) containing 10 000 spores/ml and 200 ppm of streptomycin sulfate to prevent bacterial infections are transferred to each well. Each well is then complemented with 20 µl of a suitably diluted fungicide solution. The microtitre plates are then incubated for 7 days in the dark at 20° C. Each concentration is replicated 10 times. The fungal growth of each sample is evaluated photometrically at 595 nm, and the activity of each fungicide sample is calculated using COLBY's formula.

TABLE 2a (Active ingredient IF = cyproconazole)

| Exp. No. | mg of active ingredient/l AI IF | mg of active ingredient/l AI II | Ratio I:II | E % activity, calculated [COLBY] | O % activity, found |
|---|---|---|---|---|---|
| 1 | 0.02 | — | | — | 0 |
| 2 | 0.05 | — | | — | 0 |
| 3 | 0.1 | — | | — | 0 |
| 4 | 0.2 | — | | — | 0 |
| 5 | 0.3 | — | | — | 10 |
| 6 | — | 0.01 | | — | 19 |
| 7 | — | 0.02 | | — | 26 |
| 8 | — | 0.1 | | — | 38 |
| 9 | — | 0.3 | | — | 45 |
| 10 | 0.02 | 0.01 | 2:1 | 19 | 22 |
| 11 | 0.1 | 0.01 | 10:1 | 19 | 28 |
| 12 | 0.3 | 0.01 | 30:1 | 27.1 | 31 |
| 13 | 0.05 | 0.02 | 5:2 | 26 | 29 |
| 14 | 0.1 | 0.02 | 5:1 | 26 | 33 |

TABLE 2a-continued (Active ingredient IF = cyproconazole)

| Exp. No. | mg of active ingredient/l AI IF | AI II | Ratio I:II | E % activity, calculated [COLBY] | O % activity, found |
|---|---|---|---|---|---|
| 15 | 0.2 | 0.02 | 10:1 | 26 | 32 |
| 16 | 0.1 | 0.1 | 1:1 | 38 | 43 |
| 17 | 0.2 | 0.1 | 2:1 | 38 | 46 |
| 18 | 0.3 | 0.1 | 3:1 | 44.2 | 47 |
| 19 | 0.05 | 0.3 | 1:6 | 45 | 52 |
| 20 | 0.1 | 0.3 | 1:3 | 45 | 52 |
| 21 | 0.3 | 0.3 | 1:1 | 50.5 | 60 |

TABLE 2b (Active ingredient IJ = hexaconazole)

| Exp. No. | mg of active ingredient/l AI IJ | AI II | Ratio I:II | E % activity, calculated [COLBY] | O % activity, found |
|---|---|---|---|---|---|
| 1 | 0.01 | — | — | — | 0 |
| 2 | 0.02 | — | — | — | 1 |
| 3 | 0.03 | — | — | — | 8 |
| 4 | 0.05 | — | — | — | 16 |
| 5 | 0.1 | — | — | — | 38 |
| 6 | 0.5 | — | — | — | 89 |
| 7 | — | 0.01 | — | — | 8 |
| 8 | — | 0.02 | — | — | 34 |
| 9 | — | 0.03 | — | — | 41 |
| 10 | — | 0.05 | — | — | 51 |
| 11 | — | 0.1 | — | — | 63 |
| 12 | — | 0.3 | — | — | 73 |
| 13 | — | 0.5 | — | — | 78 |
| 14 | 0.01 | 0.01 | 1:1 | 8 | 52 |
| 15 | 0.03 | 0.01 | 3:1 | 15.36 | 44 |
| 16 | 0.05 | 0.01 | 5:1 | 22.72 | 56 |
| 17 | 0.1 | 0.01 | 10:1 | 42.96 | 60 |
| 18 | 0.5 | 0.01 | 50:1 | 89.88 | 93 |
| 19 | 0.02 | 0.02 | 1:1 | 34.66 | 71 |
| 20 | 0.01 | 0.03 | 1:3 | 41 | 73 |
| 21 | 0.01 | 0.05 | 1:5 | 51 | 80 |
| 22 | 0.01 | 0.1 | 1:10 | 63 | 82 |
| 23 | 0.02 | 0.1 | 1:5 | 63.37 | 85 |
| 24 | 0.03 | 0.3 | 1:10 | 75.16 | 89 |
| 25 | 0.5 | 0.5 | 1:1 | 97.58 | 100 |

As can be seen from Tables 2a and 2b, the activity of active ingredient II can be increased markedly by adding triazole in traces which, on their own, are too small to have any effect.

EXAMPLE 3

Activity against Drechslera teres

Method:

The Drechslera teres strain is grown on V8 agar for 3 weeks at 17°–21° C. (artificial 16-hour day). The spores are washed off with sterile water and filtered, and the suspension is adjusted to a concentration of 10 000 spores/ml.

Microtitre plates with 96 wells are used. Using a Hamilton pipette, each well is filled with 180 μl of SMB medium (Sabonrand Maltose Broth) containing 10 000 spores/ml and 200 ppm of streptomycin sulfate. 20 μl aliquots of the fungicide solution to be tested are added. The plates are incubated in the dark for 5 days at 20° C.

After this period, the absorption of each well is measured photometrically at 595 nm, and the activity is calculated. Each concentration is tested in 10 replications.

TABLE 3a (Active ingredient IC = tebuconazole)

| Exp. No. | mg of active ingredient/l AI IC | AI II | Ratio I:II | E % activity, calculated [COLBY] | O % activity, found |
|---|---|---|---|---|---|
| 1 | 0.01 | — | | | 0 |
| 2 | 0.02 | — | | | 0 |
| 3 | 0.05 | — | | | 0 |
| 4 | — | 0.007 | | | 6 |
| 5 | — | 0.01 | | | 28 |
| 6 | — | 0.02 | | | 54 |
| 7 | — | 0.03 | | | 49 |
| 8 | 0.05 | 0.007 | 10:7 | 11 | 16 |
| 9 | 0.05 | 0.01 | 5:1 | 44 | 47 |
| 10 | 0.01 | 0.02 | 1:2 | 32 | 48 |
| 11 | 0.02 | 0.02 | 1:1 | 31 | 70 |
| 12 | 0.05 | 0.02 | 5:2 | 31 | 36 |
| 13 | 0.02 | 0.03 | 2:3 | 53 | 77 |
| 14 | 0.05 | 0.03 | 5:3 | 53 | 71 |

TABLE 3b (Active ingredient IF = cyproconazole)

| Exp. No. | mg of active ingredient/l AI IF | AI II | Ratio I:II | E % activity, calculated [COLBY] | O % activity, found |
|---|---|---|---|---|---|
| 1 | 0.005 | — | | — | 0 |
| 2 | 0.01 | — | | — | 0 |
| 3 | 0.02 | — | | — | 0 |
| 4 | — | 0.03 | | — | 49 |
| 5 | 0.005 | 0.03 | 1:6 | 49 | 57 |
| 6 | 0.01 | 0.03 | 1:3 | 49 | 57 |
| 7 | 0.02 | 0.03 | 2:3 | 49 | 64 |

EXAMPLE 4

Activity against Alternaria solani

Method:

The Altenaria strain is grown on 20 % V8 agar for one week in the dark at 22° C.

To test the fungicidal activity, graduated active ingredient concentrations are incorporated into the V8 agar, and its surface, in the Petri dish, is inoculated with A. solani. Each concentration is replicated 4 times. After 7 days, the radial growth of the fungus, or its inhibition, is determined.

TABLE 4a (Active ingredient IJ = hexaconazole)

| Exp. No. | mg of active ingredient/l AI IJ | AI II | I:II | E % activity, calculated [COLBY] | O % activity, found |
|---|---|---|---|---|---|
| 1 | 0.005 | — | | | 0 |
| 2 | 0.01 | — | | | 0 |
| 3 | 0.02 | — | | | 1.3 |
| 4 | — | 0.001 | | | 0 |
| 5 | — | 0.002 | | | 0 |
| 6 | — | 0.1 | | | 73.8 |
| 7 | — | 0.5 | | | 76.3 |
| 8 | — | 1.0 | | | 75.0 |
| 9 | 0.01 | 0.001 | 10:1 | 0 | 1.4 |
| 10 | 0.02 | 0.001 | 20:1 | 1.3 | 12.5 |
| 11 | 0.02 | 0.002 | 10:1 | 1.3 | 4.7 |
| 12 | 0.005 | 0.1 | 1:20 | 73.8 | 80 |
| 13 | 0.02 | 0.5 | 1:25 | 76.6 | 85 |
| 14 | 0.02 | 1.0 | 1:50 | 75.3 | 93 |

Similar, markedly increased activities are also achieved with 3-[3-(2-chlorophenyl)-2-(4-fluorophenyl)oxiran-2-ylmethyl]-1H -1,2,4-triazole (compound IE =BAS 480-F) and other triazole derivatives in the form of a mixture with 4-cyclopropyl-6-methyl-N-phenyl-2-pyrimidinamine.

Preferred mixing ratios (by weight) in these cases are:

| | |
|---|---|
| IB:II = 3:1 to 1:8 | IG:II = 3:1 to 1:12 |
| IC:II = 2:1 to 1:6 | IH:II = 3:1 to 1:8 |
| ID:II = 5:1 to 1:5 | IJ:II = 5:1 to 1:10 |
| IE:II = 2:1 to 1:8 | IK:II = 2:1 to 1:8. |
| IF:II = 5:1 to 1:10 | |

These markedly increased activities are achieved not only against powdery mildew species but also against rusts and scabs, stem break, leaf blotch (for example Septoria or net blotch species), grey mould and other pathogens.

What is claimed is:

1. A synergistic, fungicidal, two-component composition, having an effective amount of a combination of an ergosterin biosynthesis inhibitor from the triazole series as component I and a 2-anilinopyrimidine derivative as component II, wherein component I is selected from the group consisting of 1-[2-(2,4-dichlorophenyl)-4-propyl-1,3-dioxolan-2-ylmethyl]-1H-1,2,4-triazole, a propiconazole;

α-[2-(4-chlorophenyl)ethyl]-α-(1,1-dimethylethyl)-1H-1,2,4-triazol-1-ethanol also known as tebuconazole;

α-(4-chlorophenyl)-α-(1-cyclopropylethyl)-1H-1,2,4-triazol-1-ethanol also known as cyproconazole; and α-butyl-α-(2,4-dichlorophenyl)-1H-1,2,4-triazol-1-ethanol also known as hexaconazole;

or in each case a salt or metal complex thereof, and component II is 4-cyclopropyl-6-methyl-N-phenyl-2-pyrimidinamine, of the formula

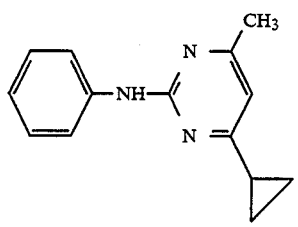

or a salt or metal complex thereof, wherein the synergistic weight ratio of component I to component II is in the range of 10:1 to 1:10, together with a carrier.

2. A composition of claim 1, wherein the I:II weight ratio is 6:1 to 1:6.

3. A composition of claim 1, wherein the I:II weight ratio is 1:1 to 1:6.

4. A composition of claim 1, wherein component I is propiconazole.

5. A composition of claim 1, wherein component I is tebuconazole.

6. A composition of claim 1, wherein component I is cyproconazole.

7. A composition of claim 1, wherein component I is hexaconazole.

8. A method of controlling fungi, which comprises treating a locus infested with, or liable to be infested with, fungi with an effective amount of an ergosterin biosynthesis inhibitor from the triazole series as component I and a synergistically effective amount of a 2-anilinopyrimidine derivative as component II, in either sequence or simultaneously, wherein component I is selected from the group consisting of 1-[2-(2,4-dichlorophenyl)-4-propyl-1,3-dioxolan-2-ylmethyl]-1H-1,2,4-triazole also known as propiconazole;

α-[2-(4-chlorophenyl)ethyl]-α-(1,1-dimethylethyl)-1H-1,2,4-triazol-1-ethanol also known as tebuconazole;

α-(4-chlorophenyl)-α-(1-cyclopropylethyl)-1H-1,2,4-triazol-1-ethanol also known as cyproconazole; and α-butyl-α-(2,4-dichlorophenyl)-1H-1,2,4-triazol-1-ethanol also known as hexaconazole;

or in each case a salt or metal complex thereof, and component II is 4-cyclopropyl-6-methyl-N-phenyl-2-pyrimidinamine, of the formula

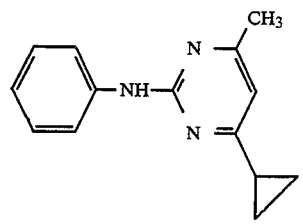

or a salt or metal complex thereof, wherein the synergistic weight ratio of component I to component II is in the range of 10:1 to 1:10.

9. A method of claim 8, wherein component I is propiconazole.

10. A method of claim 8, wherein component I is tebuconazole.

11. A method of claim 8, wherein component I is cyproconazole.

12. A method of claim 8, wherein component I is hexaconazole.

* * * * *